(12) United States Patent
Li et al.

(10) Patent No.: US 8,758,482 B2
(45) Date of Patent: Jun. 24, 2014

(54) METHODS AND COMPOSITIONS FOR REMOVING CARBON DIOXIDE FROM A GASEOUS MIXTURE

(75) Inventors: Jing Li, Cranbury, NJ (US); Haohan Wu, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 5 days.

(21) Appl. No.: 13/462,432

(22) Filed: May 2, 2012

(65) Prior Publication Data

US 2013/0042758 A1 Feb. 21, 2013

Related U.S. Application Data

(60) Provisional application No. 61/481,267, filed on May 2, 2011.

(51) Int. Cl.
*B01D 53/02* (2006.01)
(52) U.S. Cl.
USPC .................. 95/139; 95/90; 95/148; 252/182.3

(58) Field of Classification Search
USPC ............................ 95/90, 139, 148; 252/182.3
See application file for complete search history.

(56) References Cited

U.S. PATENT DOCUMENTS

| 6,989,044 | B2 * | 1/2006 | Zhang et al. ....................... 95/90 |
| 2006/0210458 | A1 * | 9/2006 | Mueller et al. ................. 422/231 |
| 2008/0121105 | A1 * | 5/2008 | Schubert et al. ................. 95/139 |
| 2010/0132549 | A1 * | 6/2010 | Yaghi et al. ..................... 95/128 |
| 2010/0186588 | A1 * | 7/2010 | Yaghi et al. ..................... 95/127 |
| 2011/0172412 | A1 * | 7/2011 | Serre et al. ..................... 540/145 |
| 2012/0167761 | A1 * | 7/2012 | Kiener et al. ..................... 95/96 |

* cited by examiner

*Primary Examiner* — Christopher P Jones
(74) *Attorney, Agent, or Firm* — Fox Rothschild LLP

(57) ABSTRACT

Provided is a method for adsorbing or separating carbon dioxide from a mixture of gases by passing the gas mixture through a porous three-dimensional polymeric coordination compound having a plurality of layers of two-dimensional arrays of repeating structural units, which results in a lower carbon dioxide content in the gas mixture. Thus, this invention provides useful compositions and methods for removal of greenhouse gases, in particular $CO_2$, from industrial flue gases or from the atmosphere.

20 Claims, 18 Drawing Sheets

A

B

C

CO₂/N₂

CO₂/CH₄

CO₂/CO

CO₂/O₂

METHODS AND COMPOSITIONS FOR REMOVING CARBON DIOXIDE FROM A GASEOUS MIXTURE

CROSS-REFERENCE TO RELATED APPLICATIONS

This application claims priority under 35 U.S.C. §119(e) to U.S. Provisional Patent Application Ser. No. 61/481,267, filed on May 2, 2011, which is hereby incorporated by reference in its entirety.

STATEMENT REGARDING FEDERALLY SPONSORED RESEARCH

The invention was made with government support under Contract No. DE-FG02-08ER46491, awarded by the Department of Energy. The U.S. government has certain rights to this invention.

FIELD OF THE INVENTION

This invention is related to the field of selective separation of one gas from a mixture of gasses, including the separation of $CO_2$ from industrial flue gases or from the atmosphere. The invention is also related to the field of microporous metal-organic framework compositions, which selectively sequester specific gas molecules, in particular $CO_2$.

BACKGROUND OF THE INVENTION

Since about 1750 human activity has increased the concentration of carbon dioxide and other greenhouse gases. Measured atmospheric concentrations of carbon dioxide are currently 100 ppmv higher than pre-industrial levels. Natural sources of carbon dioxide are more than 20 times greater than sources due to human activity, but over periods longer than a few years natural sources are closely balanced by natural sinks such as weathering of continental rocks and photosynthesis of carbon compounds by plants and marine plankton. As a result of this balance, the atmospheric concentration of carbon dioxide remained between 260 and 280 parts per million for the 10,000 years between the end of the last glacial maximum and the start of the industrial era.

It is likely that anthropogenic warming, such as that due to elevated greenhouse gas levels, has had a discernible influence on many physical and biological systems. Warming is projected to affect various issues such as freshwater resources, industry, food and health.

The main sources of greenhouse gases due to human activity are burning of fossil fuels and deforestation leading to higher carbon dioxide concentrations. Land use change (mainly deforestation in the tropics) account for up to one third of total anthropogenic carbon dioxide emissions, and farming, land use and wetland changes, pipeline losses, and covered vented landfill emissions lead to higher methane atmospheric concentrations.

The US Environmental Protection Agency (EPA) ranks the major greenhouse gas contributing end-user sectors in the following order: industrial, transportation, residential, commercial and agricultural. Major sources of an individual's greenhouse gas emissions include home heating and cooling, electricity consumption, and transportation. Corresponding conservation measures to reduce individual greenhouse gas emissions include improving home building insulation, installing geothermal heat pumps and compact fluorescent lamps, and choosing energy-efficient vehicles.

Nevertheless, a need exists for methods and compositions useful for removal of carbon dioxide from the atmosphere.

SUMMARY OF THE INVENTION

The instant invention addresses this need by providing a new method for separating the carbon dioxide present in flue gases or natural gases.

One aspect of the present invention provides a method of removing carbon dioxide from a gaseous mixture containing carbon dioxide, which includes the steps of:
(a) passing the mixture through a porous three-dimensional polymeric coordination compound characterized by a plurality of layers of two-dimensional arrays of repeating structural units, each repeating structural unit having at least one transition metal atom coordinated to:
  (1) one binding site of an exodentate bridging ligand; and
  (2) at least one binding member of a bidentate binding site on each of two polyfunctional ligands,
wherein (1) at least one binding member of a second bidentate binding site on each polyfunctional ligand is further coordinated to at least one transition metal atom in a different repeating structural unit within the same layer containing a two-dimensional array of repeating structural units; (2) the exodentate bridging ligand extends essentially perpendicularly from the plane defined by the layer containing a two-dimensional array of repeating structural units to further coordinate with a transition metal atom in a repeating structural unit in an adjacent layer; (3) the polyfunctional ligand is a ligand having at least two bidentate coordination sites; (4) the exodentate ligand is an aromatic ligand having two mono-dentate binding sites; and (5) the ligands of the porous three-dimensional polymeric compound define channels and pores of molecular size throughout the structure of the compound; and
(b) recovering the resulting mixture having a decreased carbon dioxide content.

One example of a polyfunctional ligand has a structure of Formula (I):

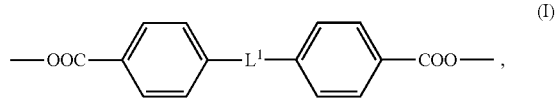

wherein $L^1$ is a bond or a linker, said linker being linear or ring, substituted or non-substituted, saturated or unsaturated group comprising between 1 and 6 atoms independently selected from the group consisting of C, N and S; and One example of an exodentate bridging ligand has the bis-pyridine structure of Formula (II):

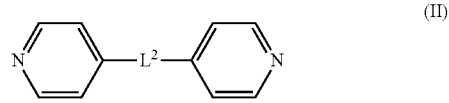

wherein $L^2$ is a bond or a linear, substituted or non-substituted, saturated or unsaturated linker containing between 2 and 6 atoms independently selected from the group consisting of C, N and S.

In another aspect, the present invention provides a method of adsorbing carbon dioxide, the method including exposing a composition containing carbon dioxide to a three-dimensional polymeric coordination compound characterized by a plurality of sheets comprising a two-dimensional array of repeating structural units, each repeating structural unit comprising at least one transition metal atom coordinated to: (a) one binding site of an exodentate bridging ligand; and (b) at least one binding member of a bidentate binding site on each of two polyfunctional ligands, wherein:

(1) at least one binding member of a second bidentate binding site on each said polyfunctional ligand is further coordinated to at least one transition metal atom in a different repeating structural unit within the same said sheet containing a two-dimensional array of repeating structural units;

(2) the exodentate bridging ligand extends essentially perpendicularly from a plane characteristic of said sheet containing a two-dimensional array of repeating structural units to further coordinate with a transition metal atom in a repeating structural unit in an adjacent sheet;

(3) the polyfunctional ligand is a ligand having at least two bidentate coordination sites; and (4) the exodentate ligand is a ligand comprises at least two monodentate binding sites, wherein the polyfunctional ligand compounds and the exodentate ligand compounds are selected so that the ligands of the three-dimensional polymeric compound define channels and pores of molecular size throughout the structure of the compound capable of adsorbing carbon dioxide.

These and other aspects of the present invention will be better appreciated by reference to the following drawings and detailed description.

DETAILED DESCRIPTION OF PREFERRED EMBODIMENTS

Figure 1:
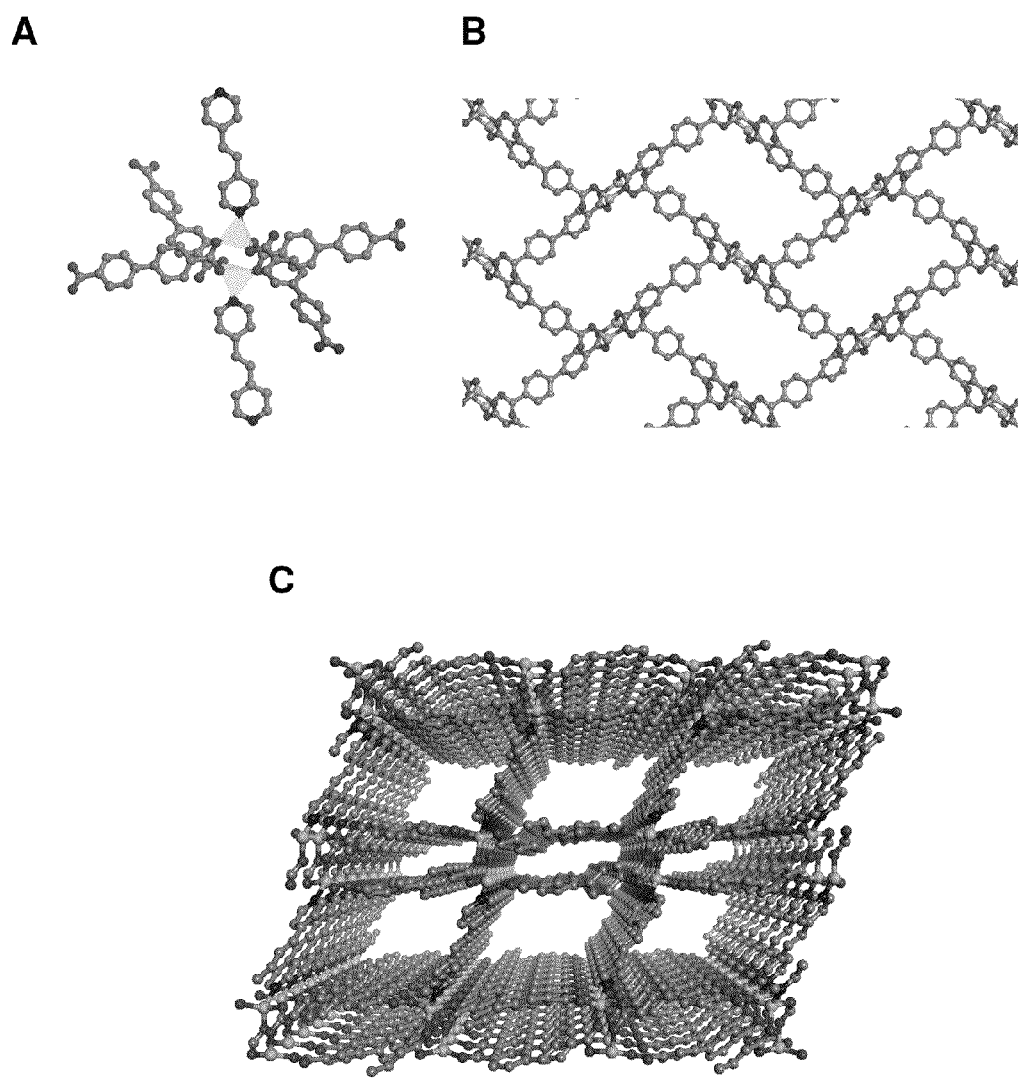
FIGS. 1A-1C show three-dimensional structure of the porous three-dimensional polymeric coordination compound according to one embodiment of the instant invention.
Figure 2A:
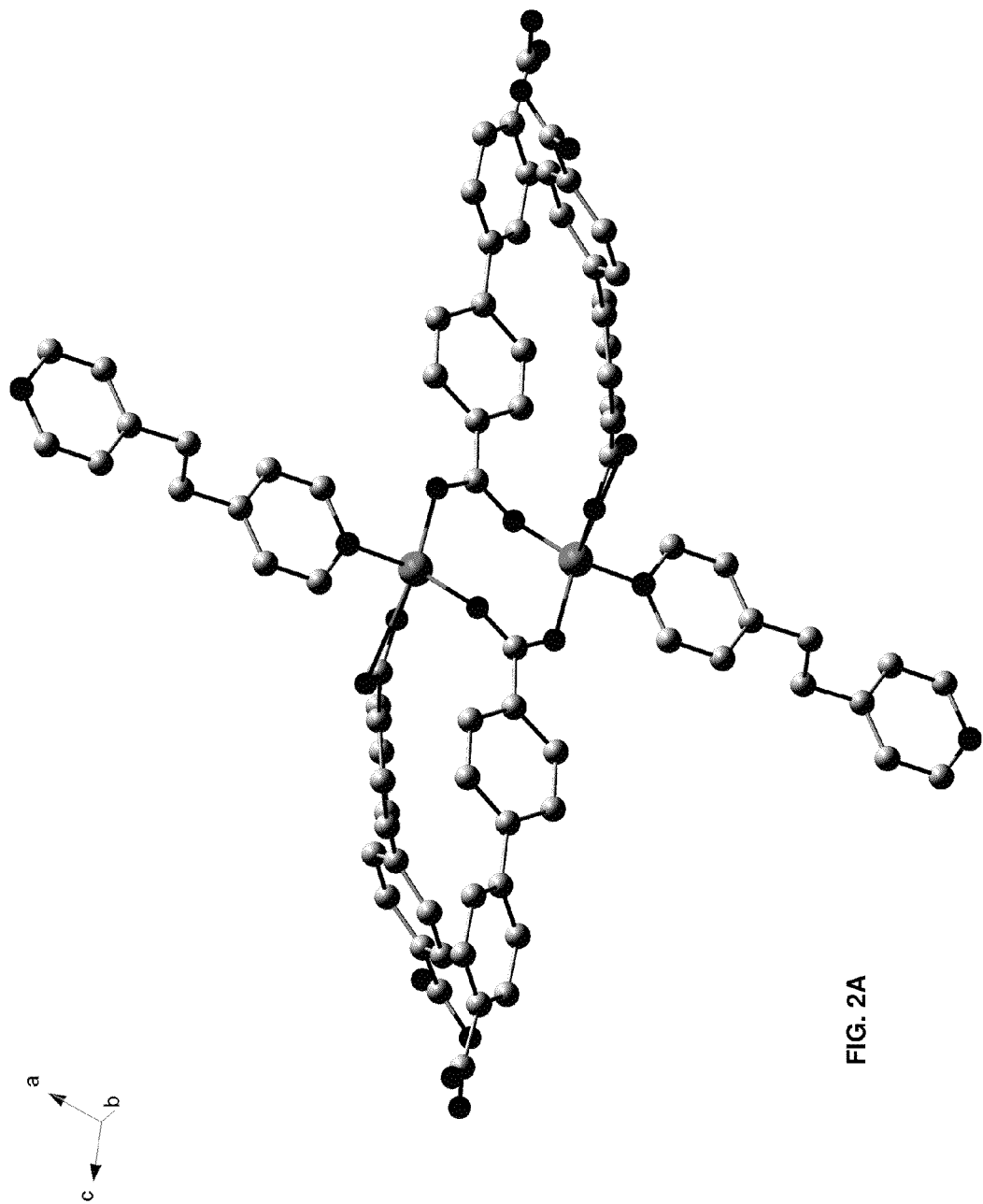
FIGS. 2A-2C show three-dimensional structure of the porous three-dimensional polymeric coordination compound according to another embodiment of the instant invention.
Figure 2B:
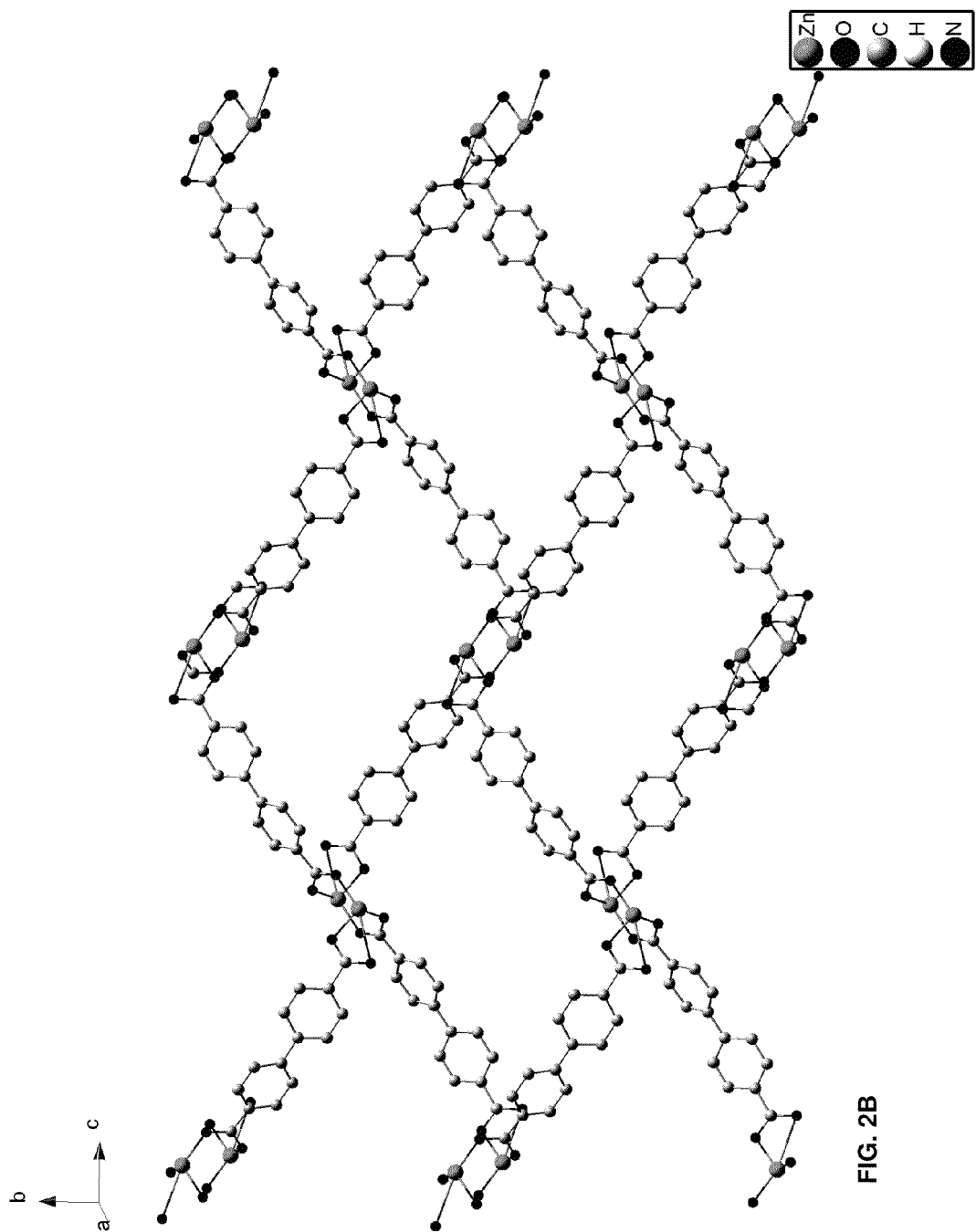
Figure 2C:
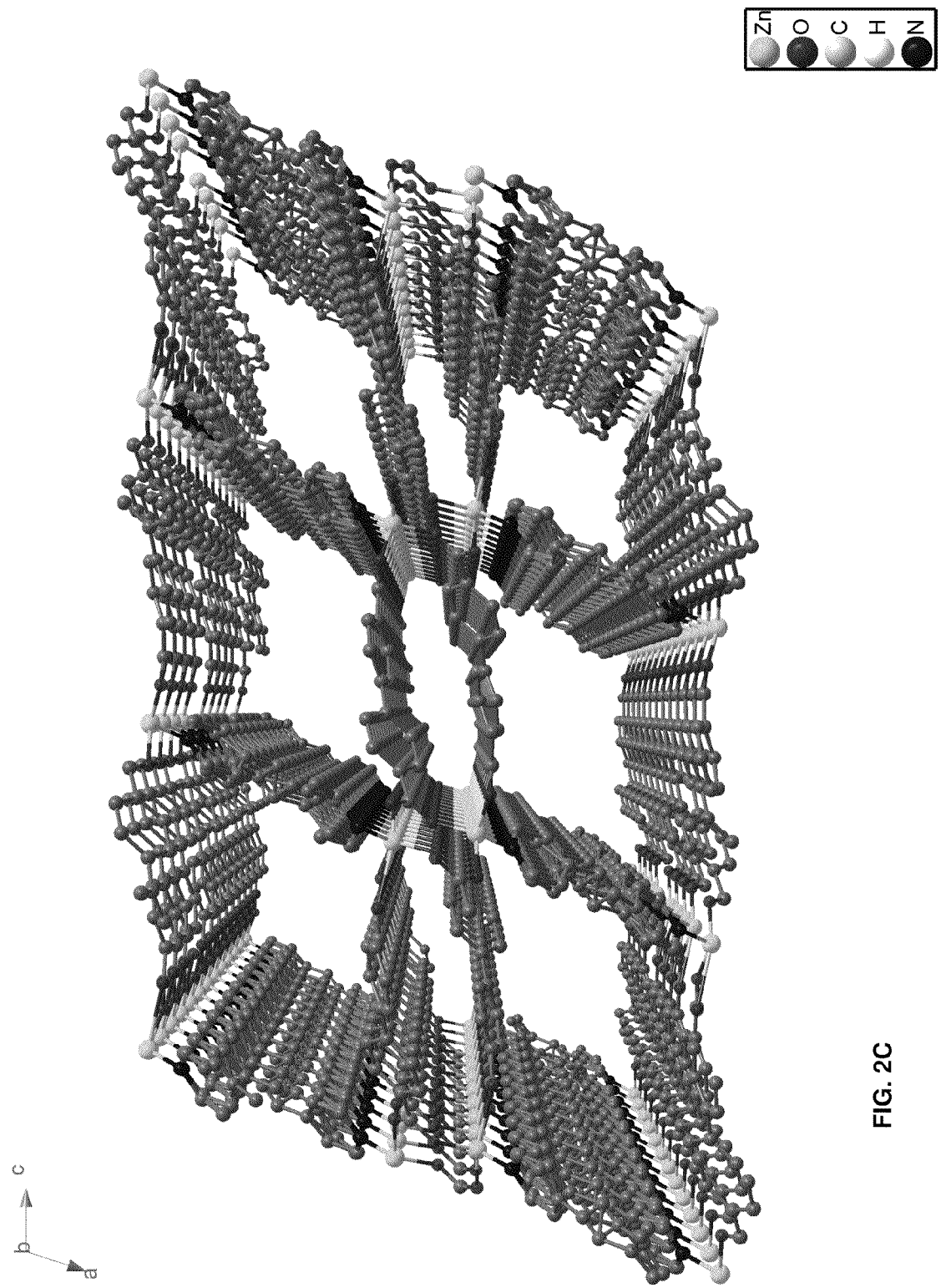

Generally, the method of the instant invention relates to adsorption of carbon dioxide and separation of carbon dioxide from a mixture of gases, e.g., a mixture of carbon dioxide and one or more of other gases, including but not limited to $O_2$, $N_2$, $CO$, $H_2$ and $CH_4$, using microporous three-dimensional polymeric coordination complex materials. These polymeric coordination complexes were in part described in U.S. patent application Ser. No. 10/718,047 (Publication No. 2004/0110950) and U.S. patent application Ser. No. 12/824,008, both of which are hereby incorporated by reference in their entirties.

Porous materials according to the present invention are three-dimensional polymeric coordination compounds characterized by a plurality of layers of essentially two-dimensional arrays of repeating structural units, each repeating structural unit having at least one transition metal atom coordination bonded to one binding site of an exodentate bridging ligand and at least one binding member of a bidentate binding site on each of two polyfunctional ligands.

In one aspect the present invention provides a method of separating carbon dioxide from a mixture of gases, the method comprising the steps of:

a) passing the gas mixture through a porous three-dimensional polymeric coordination compound characterized by a plurality of layers comprising two-dimensional arrays of repeating structural units, each repeating structural unit comprising at least one transition or post-transition metal atom or cation coordinated to:

(1) at least one binding member of a bidentate binding site on each of two polyfunctional ligands of Formula I:

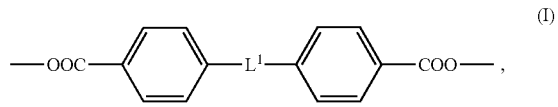

(I)

wherein $L^1$ is a bond or a linker, said linker being linear or ring, substituted or non-substituted, saturated or unsaturated group comprising between 1 and 6 atoms independently selected from the group consisting of C, N and S; and (2) one binding site of a bis-pyridine exodentate bridging ligand of Formula II:

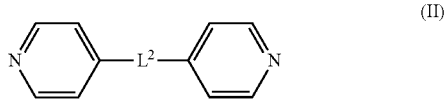

wherein $L^2$ is a bond or a linear, substituted or non-substituted, saturated or unsaturated linker containing between 2 and 6 atoms independently selected from the group consisting of C, N and S; and wherein:
(i) at least one binding member of a second bidentate binding site on each polyfunctional ligand is further coordinated to at least one transition metal atom or cation in a different repeating structural unit within the same layer containing a two-dimensional array of repeating structural units;
(ii) the exodentate bridging ligand extends essentially perpendicularly from a plane defined by said layer containing a two-dimensional array of repeating structural units to further coordinate with a transition metal atom in a repeating structural unit in an adjacent layer; and
(iii) the ligands of the three-dimensional polymeric compound define channels and pores of molecular size throughout the structure of the compound; and b) recovering the resulting mixture, wherein the resulting mixture has a decreased carbon dioxide content.

In one embodiment, $L^1$ and $L^2$ are each independently a bond, —CH=CH— or —CH$_2$—CH$_2$—.

In one embodiment, $L^1$ is a bond; and $L^2$ is —CH=CH— or —CH$_2$—CH$_2$—.

In one embodiment, the transition metal is zinc.

In one embodiment, the step (a) is conducted at a pressure of greater than 0.1 atm.

In one embodiment, the step (a) is conducted at a pressure of about 1 atm.

In one embodiment, the mixture of gases contains at least one gas selected from the group consisting of hydrogen, oxygen, nitrogen, carbon monoxide, and methane.

In one embodiment, the mixture of gases is an industrial flue gas.

In one embodiment, the method further includes a step of (c) recovering carbon dioxide retained in the microporous three-dimensional polymeric coordination compound.

In one embodiment, the recovering step includes heating the polymeric coordination compound containing carbon dioxide to an elevated temperature until the carbon dioxide is released, and collecting the carbon dioxide released from the polymeric coordination compound.

In one embodiment, the method includes repeating step (a) until the carbon dioxide content in the mixture is reduced to a desired level.

In another aspect, the present invention provides a method of adsorbing carbon dioxide, the method including exposing a composition containing carbon dioxide to a three-dimensional polymeric coordination compound characterized by a plurality of sheets comprising a two-dimensional array of repeating structural units, each repeating structural unit comprising at least one transition metal atom coordinated to: a) one binding site of an exodentate bridging ligand; and b) at least one binding member of a bidentate binding site on each of two polyfunctional ligands, wherein:

(1) at least one binding member of a second bidentate binding site on each said polyfunctional ligand is further coordinated to at least one transition metal atom in a different repeating structural unit within the same said sheet containing a two-dimensional array of repeating structural units;
(2) the exodentate bridging ligand extends essentially perpendicularly from a plane characteristic of said sheet containing a two-dimensional array of repeating structural units to further coordinate with a transition metal atom in a repeating structural unit in an adjacent sheet;
(3) the polyfunctional ligand is a ligand having at least two bidentate coordination sites; and
(4) the exodentate ligand is a ligand comprises at least two monodentate binding sites, wherein the polyfunctional ligand compounds and the exodentate ligand compounds are selected so that the ligands of the three-dimensional polymeric compound define channels and pores of molecular size throughout the structure of the compound capable of adsorbing carbon dioxide.

In one embodiment, the repeating structural unit of the compound has the stoichiometric formula $[M_a(pbd)_b(ed)_f]$, optionally comprising one or more solvent molecules characterized by formula $[M_a(pbd)_b(ed)_f]\cdot n(sol)$, wherein:
"pbd" is a polyfunctional ligand having at least two bidentate binding sites;
"ed" is an exodentate ligand having at least two monodentate binding sites;
"M" is a transition or post-transition metal having at least one stable oxidation state capable of forming stable bonds with said polyfunctional and exodentate ligands;
"sol" is a solvent molecule;
"a", "b", and "f" are independently integers selected from 1 to 3;
n is a number between 0-3; and
the coordinate space occupied by the "pbd" and "ed" ligands is equal to a stable coordination number of "a" number of transition or post-transition metal (M) atoms or cations.

In one embodiment, the polyfunctional ligand is a ligand having two bidentate binding sites, and wherein the exodentate ligand is a ligand having two monodentate binding sites.

In one embodiment, the polyfunctional ligand is a biaryl-dicarboxylate of formula I:

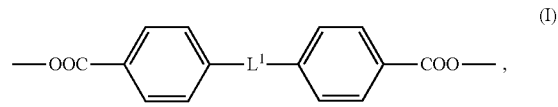

wherein $L^1$ is a bond or a linker, the linker being linear or ring, substituted or non-substituted, saturated or unsaturated group comprising between 1 and 6 atoms independently selected from the group consisting of C, N and S.

In one embodiment, $L^1$ is a bond, —CHR$^1$—, —CHR$^1$—CHR$^2$—, —CR$^1$=CR$^2$—, or —C≡C—, wherein R$^1$ and R$^2$ are each independently hydrogen (H), halogen, hydroxyl, or methyl.

In one embodiment, the exodentate bridging ligand is a bis-pyridine compound of Formula II:

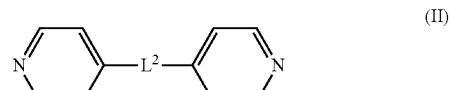

wherein $L^2$ is a bond or a linear, substituted or non-substituted, saturated or unsaturated linker containing between 1 and 6 atoms independently selected from the group consisting of C, N and S, wherein the nitrogen (N) atoms of the two pyridine rings are two binding sites.

In one embodiment, $L^2$ is a bond, —CHR$^2$—, —CHR$^1$—CHR$^2$—, —CR$^1$=CR$^2$—, or —C≡C—, wherein R$^1$ and R$^2$ are each independently hydrogen (H), halogen, hydroxyl, or methyl.

In one embodiment, "M" is zinc or cadmium, "pbd" is biphenyl-4,4'-dicarboxylate ("bpdc"), "ed" is selected from 4,4'-bipyridine ("bp"), 1,2-bis(4-pyridyl)ethylene ("bpee") or 1,2-bis(4-pyridyl)ethane ("bpe"), "sol" is dimethylformamide (DMF), "a" is 2, "b" is 2, "f" is 1, and n is 0 or 2.

In one embodiment, "M" is $Zn^{2+}$, "pbd" is biphenyl-4,4'-dicarboxylate ("bpdc"), "ed" is 1,2-bis(4-pyridyl)ethylene ("bpee"), "Sol" is dimethylformamide (DMF), "a" is 2, "b" is 2, "f" is 1, and n is 2, wherein the compound comprises a flexible, porous three-dimensional network composed of one-dimensional open channels running along crystallographic b-axis.

In the repeating structural units the transition metal atom has coordination sites arranged geometrically about it. For example, an octahedral arrangement of coordination sites has four coordination sites located in a plane, equidistant from the metal center (occupying the corners of a square, the metal centered in the square), and two additional coordination sites, one located above and one below the plane, centered over the metal center. A second example is a trigonal bipyramidal arrangement of coordination sites, which involves three coordination sites in a plane equidistant from a metal center (occupying the corners of an equilateral triangle, metal centered in the triangle) with two additional coordination sites, one located above and one below the plane and centered over the metal.

In coordination compounds, the coordination sites about the metal center are occupied by ligands. Ligands can be atoms, molecular fragments, or molecules, with or without an electron charge. Ligands have binding sites. A ligand binding site is an atom or group of atoms in close proximity on the ligand that interact with one or more coordination sites of the metal center.

The number of coordination sites on a metal center which can be occupied by a given binding site of a ligand is the ligand's dentate number. Thus, a ligand having a binding site which can only occupy one coordination site on a metal center is monodentate, a ligand having a binding site which can occupy two coordination sites on a metal center is bidentate, and so forth.

Polydentate binding sites, for example a bidentate binding site, are essentially a group of monodentate binding sites arranged in a ligand such that they can interact simultaneously with multiple coordination sites on one metal center. This is to say that a bidentate binding site has two atoms which can interact with a metal center to form a coordinate bond and are in sufficiently close proximity and geometrically disposed such that both atoms of the bidentate ligand binding site can participate in the occupation of two coordination sites (one atom in each site) of a single metal atom. Alternately the binding members can occupy one coordination site on each of two metal atoms in close proximity.

Examples of such ligands are those containing a carboxylate, phosphate, sulfate, nitrate, diamino, or amide functional groups. It will be appreciated that other types of binding sites comprising oxygen and/or nitrogen atoms arranged such that two of either atoms are proximate and properly geometrically disposed to each other will also constitute bidentate binding sites.

As used herein, each atom of a polydentate binding site on a ligand is referred to as a coordinating member of that binding site. Further, as used herein, a polydentate binding site on a ligand is distinct from a ligand which has multiple monodentate binding sites for example, an exodentate ligand, further described below.

A ligand with multiple monodentate binding sites can interact with a single coordination site on several different transition metal centers at the same time, but it can not interact with more than one coordination site on a single metal center at one time. For example, the oxygen atoms of a dicarboxylate group constitute a bidentate binding site with each oxygen atom constituting a coordinating member of that binding site, and the nitrogen atoms of 4,4'-bipyridine constitute two monodentate binding sites in the bipyridine ligand. The oxygen atoms of the dicarboxylate binding site are geometrically disposed so that both can simultaneously interact with a different coordination site on a single transition metal center but 4,4'-bipyridine cannot be distorted to bring both nitrogen atoms into the geometrical alignment necessary for both nitrogen atoms to simultaneously interact with two coordination sites on one transition metal.

As mentioned above, the porous, three-dimensional compounds of the present invention are formed of layers, each characterized by a two-dimensional array of repeating structural units that are interbonded by exodentate ligands coordinated between two transition metal atoms, each located in a repeating structural unit in an adjacent layer. Each two-dimensional array layer of repeating structural units has transition metal centers bonded together by polyfunctional ligands. The polyfunctional ligands extend in two directions, e.g., the x and y axis of a plane defining the two dimensional array layer, and form coordination bonds between transition metal centers in two different repeating structural units using coordinating members of two different polydentate sites on the ligand (thus, an essentially two-dimensional array of repeating structural units).

The planarity of the layer itself can vary with respect to the alignment and bond angles of the constituents of the repeating structural units. It will be appreciated that the term layer includes a range of structural configurations ranging between a strictly planar arrangement of the constituents of the layer to an arrangement in which the constituents can be above and below a plane defined by the layer by a distance on the order of a dimension of a repeating structural unit.

The structure of the polymeric coordination compounds of the present invention extends in a third direction, e.g. along a z axis perpendicular to the x, y plane described above, by co-ordination bonding of exodentate ligands. The exodentate ligands extend essentially perpendicularly from the plane defined by the two-dimensional array of repeating structural units along the z axis to form bonds between the transition metal atoms of two adjacent layers of two-dimensional arrays of repeating structural units using two different monodentate binding sites on the ligand, thus forming a bridge bonding together adjacent two-dimensional array layers of repeating structural units.

The properties of transition metal compounds and of the metal atom(s) and coordinated ligands comprising such compounds are often described in terms of the hard, soft, or borderline acid or base character of the transition metal and its ligands. This concept is described, for example, by Pearson in *Mechanisms of Inorganic Reactions, a Study of Metal Complexes in Solution*, (Wiley & Sons, New York, 1967), and in

*Inorganic Chemistry, Principles of Structure and Reactivity*, (3rd Ed., James E. Huheey). Not being bound by theory, transition metal atoms suitable for use in compounds of the present development are selected from transition metals having at least one stable oxidation state classified under the Pearson categories as a soft or borderline acid, for example, iron, cobalt, nickel, zinc, cadmium, palladium, and platinum in the +2 oxidation state, and which are capable of forming (in any oxidation state) stable complexes with ligands classified under the Pearson categories as hard or borderline bases, for example, those which include in their structure one or more nitrogen or oxygen atoms that are available for coordination to a metal center.

The polyfunctional ligand compounds suitable for use in the compounds of the present invention have at least one ligand containing at least two bidentate binding sites disposed in the ligand structure. The bidentate sites of suitable polyfunctional ligand compounds are positioned so that if each of two different transition metal centers are bonded to one bidentate binding site, the resulting structure has an essentially co-linear arrangement of the ligand and metal atoms with the metal atoms located between about 4 angstroms and about 20 angstroms apart.

Further, suitable polyfunctional ligand compounds are characterized as being "rigid," and therefore not capable of having a conformation that provides for close proximity of these two bi-dentate binding sites. Ligands having in their structure more than two binding sites are also contemplated, provided that at least two binding sites are bidentate and arranged to give an essentially co-linear disposition of the ligand and two metal atoms bound to the bidentate binding sites.

Preferably, the polyfunctional ligand compound used in the pillared, porous, three-dimensional polymeric coordination compounds of the present development have only two bidentate binding sites, but ligands having more than two bidentate binding sites are contemplated, as well as those which have polydentate binding sites and additionally, one or more monodentate binding sites. An example of a polyfunctional ligand compound suitable for use in compounds of the present development is biphenyl-4,4'-dicarboxylate.

The porous three-dimensional polymeric compounds of the present invention can be described as pillared compounds, with exodentate ligand pillars bonding layers of two-dimensional arrays of repeating structural units together. Exodentate ligands are compounds having at least two mono-dentate binding sites, which are disposed in the ligand compound structure such that two different metal atoms, one bonded to each binding site, and the remaining ligand compound structure are essentially co-linear. Suitable exodentate ligand compounds are also characterized as having a rigid or semi-rigid structure, which means that they cannot assume a conformation that places the two binding sites proximal to each other.

The binding sites of exodentate ligand compounds suitable for use in compounds of the present invention are characterized in terms of the Pearson categories described above as hard or borderline bases and are further characterized as "good pi-backbonding ligands," as that term is defined in *Principles and Applications of Organotransition Metal Chemistry*, (Coleman and Hegedus, University Science Books, Mill Valley, CA. 1980). An example of a suitable exodentate bridging ligand compound is 4,4'-bipyridine, wherein the pyridine moieties are connected by a spacer or a linker between the C1 atoms of pyridine moieties.

Generally, the linker is a relatively short structure that may be represented as two to five groups linked in a linear arrangement (e.g. $R^1$-$R^2$-$R^3$-$R^4$-$R^5$), with two groups being the most preferable linker length. The groups $R^1$, $R^2$ and, if present, $R^3$-$R^5$, can be selected from $CH_n$, wherein n is 1 or 2, $NH_m$, wherein m is 0 or 1, or S, and can form single, or, in some embodiments, double or triple bonds with the adjacent moieties. The linker can also be substituted. When the linker is unsaturated, the unsaturation may comprise double and/or triple bonds. When the unsaturation comprises a double bond, the geometry of the linker may be either cis or trans. Preferably, R is —CH=CH— or —$CH_2$—$CH_2$—. Preferably, the geometry of —CH=CH— is trans. Stated another way, the linker, or bridge, is a straight-chained, non-branched, substituted or unsubstituted moiety containing from two to five atoms selected from C, N and S.

Thus, the porous three-dimensional compound of the instant invention contains layers of a polyfunctional ligand such as, for example, biphenyl-4,4'-dicarboxylate forming coordination bonds with a transitional metal, with cobalt and zinc being the most preferred transition metals for use in polymeric compounds of the present invention.

The layers of the polyfunctional ligand are connected through exodentate ligand pillars, which also form coordination bonds with the transitional metal, thereby forming a porous three-dimensional layered structure containing channels or pores of molecular size.

Because of its properties, the porous material of the instant invention can adsorb carbon dioxide much more efficiently than other small gases, such as nitrogen, oxygen, carbon monoxide, hydrogen and methane. Therefore, after passing through the layer of the three-dimensional porous material, the resulting mixture will have a diminished content of carbon dioxide compared to the original mixture.

The method of the instant invention may be conducted under a variety of parameters. Non-limiting examples of pressure suitable for use with the instant invention are greater than about 0.1 atm, e.g., about 0.2 atm or greater, about 0.3 atm or greater, about 0.4 atm or greater, about 0.5 atm or greater, about 0.6 atm or greater, about 0.7 atm or greater, about 0.8 atm or greater, about 0.9 atm or greater, about 1.0 atm or greater, and the like. For flue gas separation, the partial pressure is typically between about 0.1 and about 0.2 atm.

Temperatures suitable for conducting the instant method can also vary, e.g., from between about 20° C. to about 200° C. and higher, including, without limitation, about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., and so forth. The compound of FIG. 1C is stable at temperatures at least as high as 200° C. For flue gas separation, the temperature is typically between about 20 and about 60° C.

After the process has been performed once it can be repeated if necessary, e.g., by passing the resulting mixture through the second layer of the three-dimensional porous material, thus further depleting the mixture of the carbon dioxide.

In different embodiments of the invention the carbon dioxide content decreases by at least 5%, or at least 10% or at least 15%, or at least 20% or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or about 99% of the original mixture.

The term "post-transition metal", as used herein, refers to the metallic elements to the right of the transition elements on the periodic table, for example, aluminum, gallium, germanium, indium, tin, lead, bismuth, etc.

Figure 14:
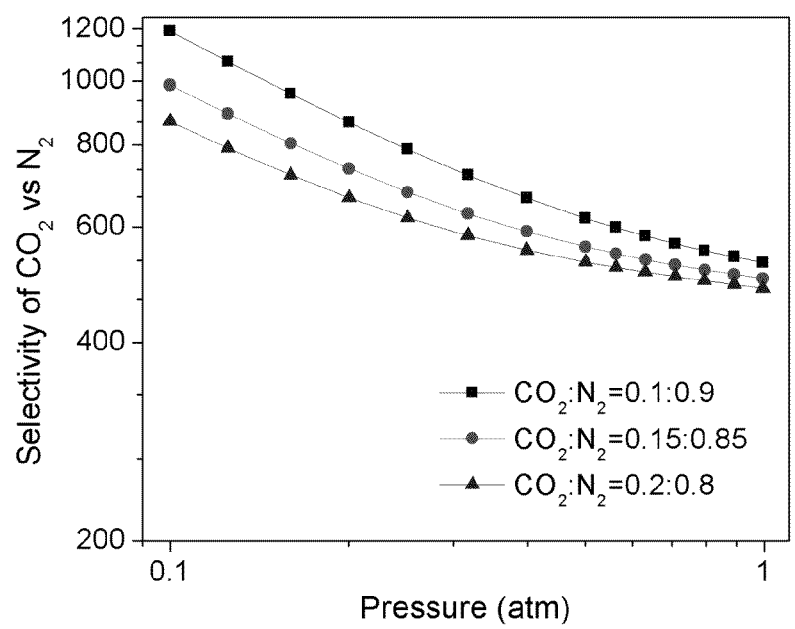
FIG. 14 illustrates adsorption selectivity of $CO_2$ over $N_2$ at room temperature (298K) at different compositions in a binary gas mixture as calculated according to ideal adsorbed solution theory (IAST).

One compound according to the present invention, $Zn_2$(bpdc)$_2$(bpee)·2DMF, which is depicted in FIG. 1C (bpdc=4,4'-biphenyl dicarboxylate, bpee=1,2-bis(4-pyridyl)ethylene), exhibits very high adsorption selectivity of $CO_2$ over other small gases under such conditions, with separation ratios of 294, 190, 257 and 441 (v/v) for $CO_2$:$N_2$, $CO_2$:$H_2$, $CO_2$:$CH_4$ and $CO_2$:CO, respectively, at 0.16 atm and 25° C. measured as single gas adsorption ratios. Breakthrough experiments on mixtures that mimic industrial flue gas (20% $CO_2$ in dry air) demonstrate high selectivity and separation capability of this material. The adsorption selectivity of $CO_2$ over $N_2$ at room temperature (298K) at different compositions in a binary gas mixture are calculated according to the ideal adsorbed solution theory (IAST), as illustrate in FIG. 14 (for more on IAST; see Myers, A. L.; Prausnitz, J. M., *AIChE. J.*, 1965, 11, 121. Chowdhury, P.; Bikkina, C.; Gumma, S., *J. Phys. Chem. C*, 2009, 113, 6616, Bae, Y. S., et. al., *Langmuir*, 2008, 24, 8592). To the best of our knowledge, the IAST adsorption selectivity of $CO_2$ over $N_2$ in a binary gas mixture at 298K represents the highest values reported to date.

Figure 4A:
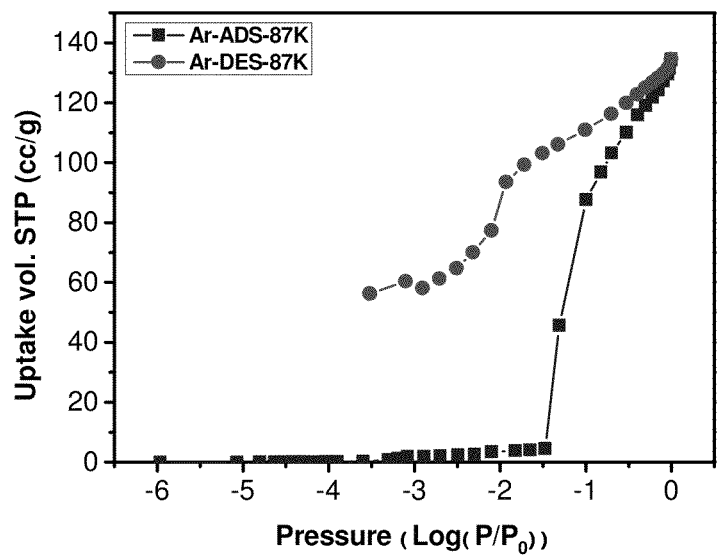
FIGS. 4A and 4B respectively demonstrate Ar and $N_2$ adsorption-desorption isotherms at 87 and 77K, respectively.
Figure 4B:
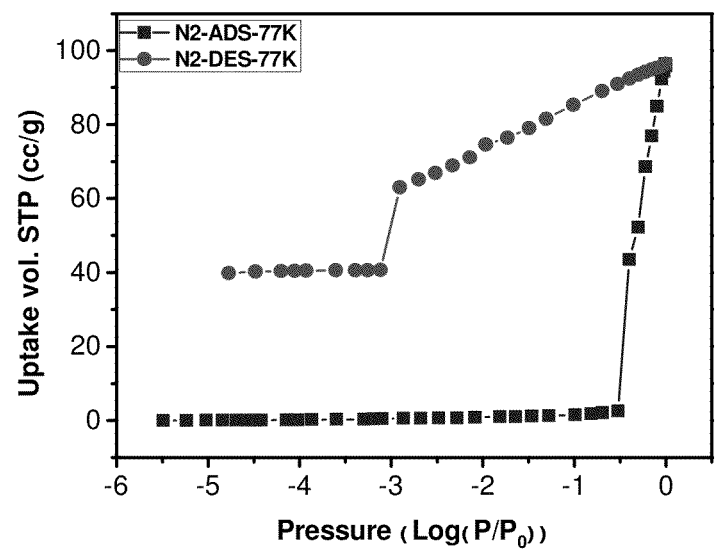

The structure of $Zn_2$(bpdc)$_2$(bpee)·2DMF is a flexible, porous three-dimensional (3D) network composed of one-dimensional (1D) open channels running along the crystallographic b-axis. The size of the parallelogram shaped pore window is ~5×7 Å (excluding van der Waals radius of carbon, 1.7 Å). The solvent accessible volume was calculated to be 1171.9 Å$^3$ (27.6% of the unit cell volume) and the micropore volume, 0.171 cc/g based on the 77K $N_2$ adsorption isotherm data (See FIGS. 4A and 4B). The structure is highly flexible and undergoes a fully reversible change after removal and refill of DMF guest molecules (See FIGS. 5 and 6). This high structural flexibility leads to a well documented gate opening-closing phenomenon, as evident in both Ar and $N_2$ isotherms at 87 and 77K, respectively.

To examine the separation capability of this flexible compound, single component gas sorption experiments were carried out on $H_2$, $CO_2$, CO, $CH_4$, and $N_2$ near room temperature and up to 1 atm. At 25° C., the $CO_2$ shows a little adsorption at low pressure. An abrupt increase is observed as the pressure reaches ~0.1 atm, which is followed by a quick increase to a maximum uptake of 25 cc/g at 1 atm (FIGS. 3A-3D). Unlike previously reported structures that exhibit gate opening/closing phenomena, the desorption curve nearly retraces the adsorption one, showing practically no hysteresis. Repeated experiments confirmed this observation (See FIG. 7). This type of isotherm is quite unusual, and has rarely been reported.

Adsorption isotherms of $N_2$ were measured under the same conditions and the results indicate very little uptake over the entire pressure range. (FIG. 3A) The $CO_2$/$N_2$ selectivity is calculated to be 294:1 at 0.16 atm and 25° C. and 116:1 at 1 atm. To the best of our knowledge, this represents the highest separation ratio known to this date. In addition, $H_2$, $CH_4$ and CO adsorption-desorption isotherms were performed under identical experimental conditions (25° C. and up to 1 atm) and all show very similar behavior as that of $N_2$ (See FIGS. 3B-3D). The selectivity ratios of $CO_2$ over $H_2$, $CH_4$ and CO are 190, 257 and 440, respectively, at 0.16 atm and 25° C.

Figure 9:
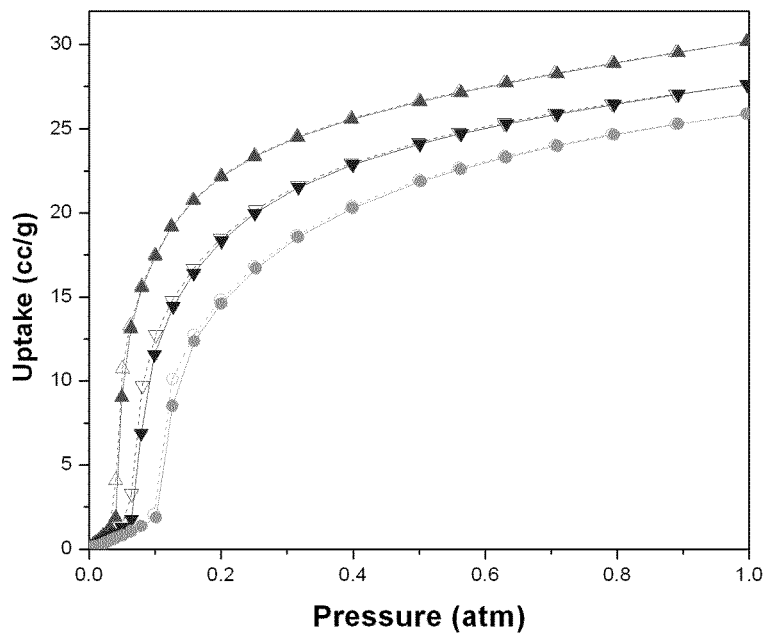
FIG. 9 depicts $CO_2$ adsorption-desorption isotherms at 5° C. (red), 15° C. (blue) and 25° C. (green), wherein adsorption and desorption data are represented by filled and open symbols, respectively.

The extent of adsorbent-adsorbate interactions was estimated by the heats of $CO_2$ adsorption calculated based on the sorption isotherms obtained at 5, 15 and 25° C. As shown in FIG. 9, the values are 28.5-28.9 and 32.5-33.5 kJ/mol, respectively, before and after the onset pressure of the gate opening, indicative of strong interactions between the framework and the $CO_2$ quadruple moment ($-1.4 \times 10^{-39}$ cm$^2$) and additional electrostatic interactions after the gate is opened.

Figure 10:
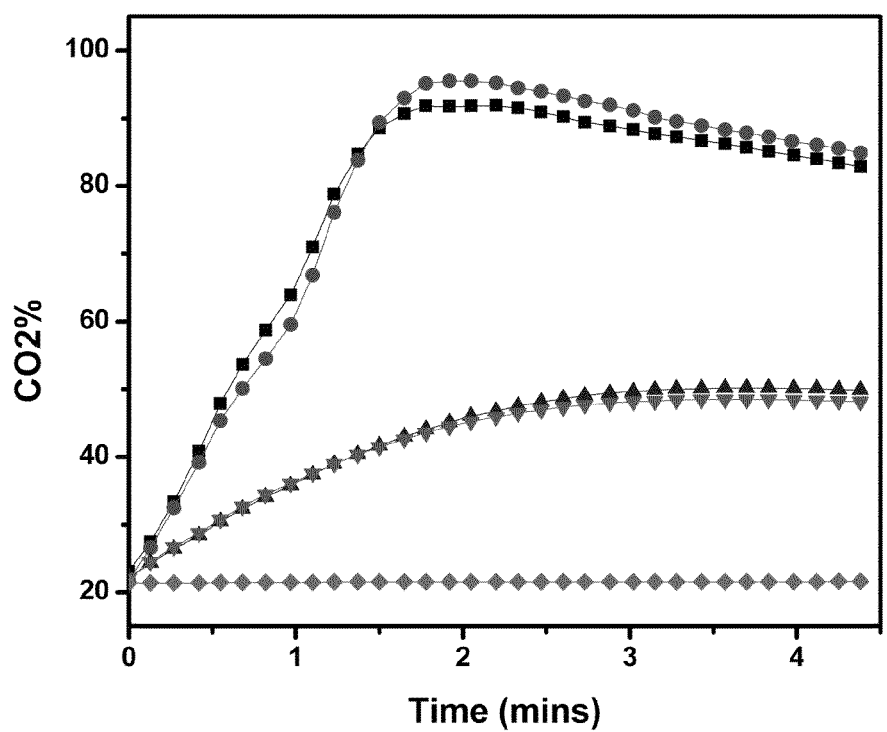
FIG. 10 depicts the $CO_2$ composition (vol %) of exhaust from an activated (i.e., absorbed by a guest-free or $CO_2$-free) compound according to FIG. 1 at 25° C. (blue and cyan, two separate runs) and 50° C. (black and red), in comparison with the values from an as-made sample at 25° C. (pink). The initial feed concentration of $CO_2$ is ~20%.

The compound of FIG. 1C was tested in a more real-world process using a gas mixture mimicking industrial flue gas compositions. FIG. 10 illustrates exhaust gas composition during the desorption phase of one cycle. At a $CO_2$ feed concentration of 20%, the activated compound re-leased a maximum of 50% and 95% of $CO_2$ at 25 and 50° C. within 3 and 2 minutes, respectively. These values correspond to 2.5 and 4.75 times of the feed concentration, after a single cycle. The maximum separation ratio of $CO_2$/$N_2$ of this mixture gas was calculated to be 84 at 50° C.

The recycleability of the samples were further examined by repeating the breakthrough experiment under identical conditions after the initial run. The results for both 25 and 50° C. runs are plotted in FIG. 10. Data clearly suggest that the process is highly reproducible.

EXAMPLES

1. Synthesis of Polymeric Coordination Complexes (A) Synthesis of $Zn_2$(BPDC)$_2$(BPEE)·2DMF Crystals of $Zn_2$(BPDC)$_2$(BPEE)·2DMF (FIG. 1C) were solvothermally synthesized by mixing $Zn(NO_3)_2$·6$H_2O$ (0.0892 g, 0.30 mmol), 4,4-biphenyldicarboxylic acid ($H_2$BPDC, 0.0727 g, 0.30 mmol) and 1,2-bis(4-pyridyl)ethylene (BPEE), 0.0547 g, 0.30 mmol) at molar ratio of 1:1:1 in 15 mL of DMF. The reaction container was heated at 165° C. for 3 days and cooled down to room temperature at the rate of 0.1° C./min. Colorless block-like crystals (0.0657 g, 47% yield) were obtained by filtering, washing by DMF three times and drying in vacuum oven.

(B) Synthesis of $Zn_2$(BPDC)$_2$(BPE)·2DMF $Zn_2$(BPDC)$_2$(BPE)·2DMF was prepared in an analogous manner by substituting 1,2-bis(4-pyridyl)ethane (BPE) for the 1,2-bis(4-pyridyl)ethylene (BPEE). The reaction mixture was heated at 170° C. for 3 days, and the product recovered as described above.

2. Adsorption Experiments

All gas sorption experiments were performed on a volumetric gas sorption analyzer (Autosorb-1 MP, Quantachrome Instruments). Liquid nitrogen and liquid argon were used as coolant to achieve cryogenic temperatures (77 and 87 K). Ultra high purity Ar (99.995%) and $H_2$, $N_2$, CO, $CO_2$, and $CH_4$ (99.999%) were used. The Ar and $N_2$ sorption isotherms were collected in a relative pressure range from $10^{-6}$ to 1 atmosphere at 87 and 77K, respectively. The initial out-gassing process for each sample was carried out at 408K for over-night (under vacuum). Out-gassed samples in the amount of ~85-90 mg were used for gas sorption measurements and the weight of each sample was recorded before and after out-gassing to confirm the removal of guest molecules.

Figure 3A:
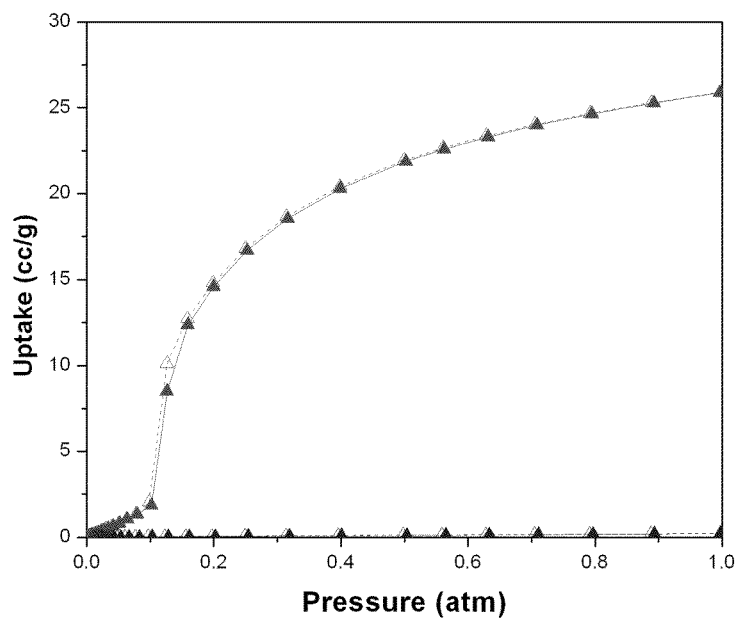
FIGS. 3A-3E demonstrate selectivity of this compound for $CO_2$ versus $N_2$, $CH_4$, $CO$, $O_2$ and $H_2$, respectively.
Figure 3B:
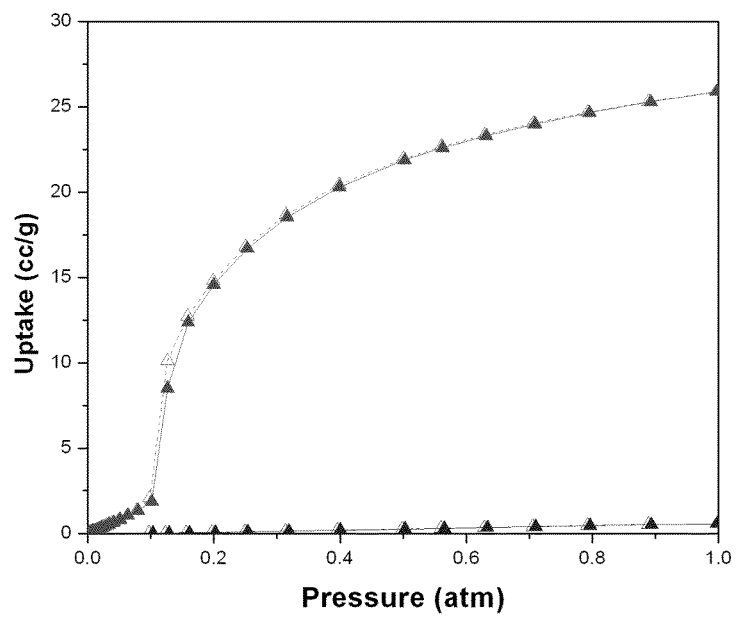
Figure 3C:
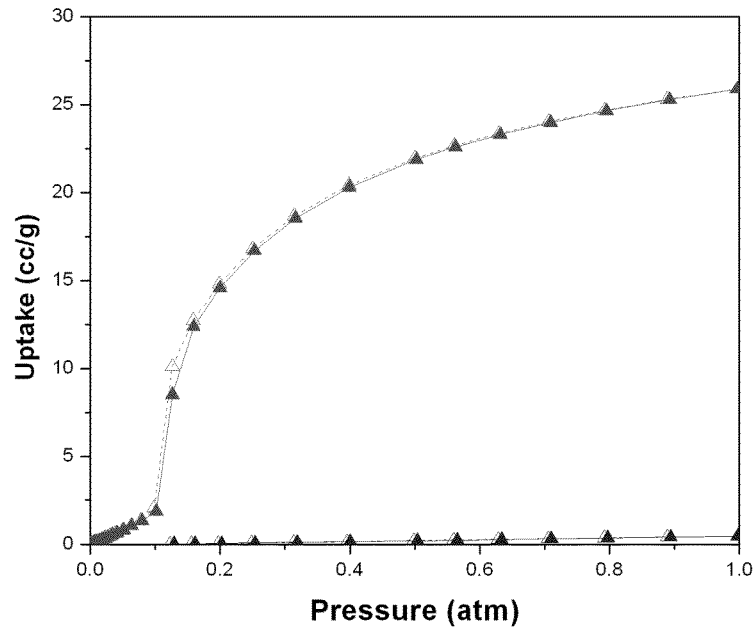
Figure 3D:
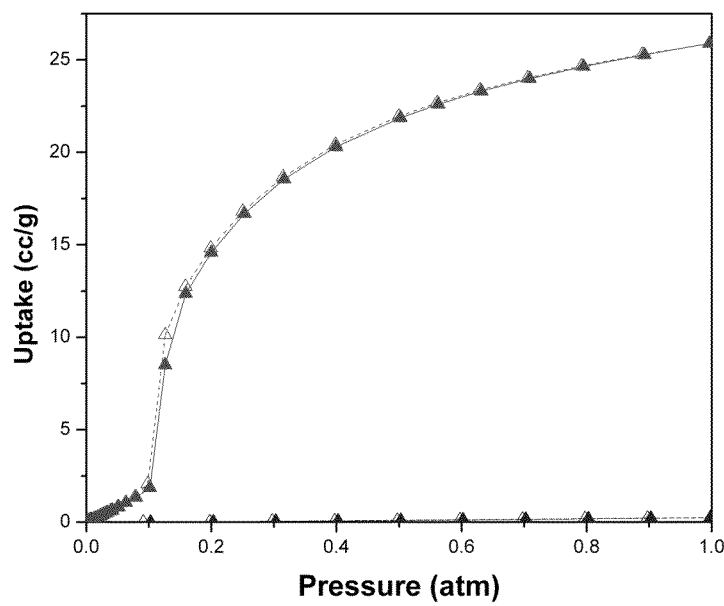
Figure 3E:
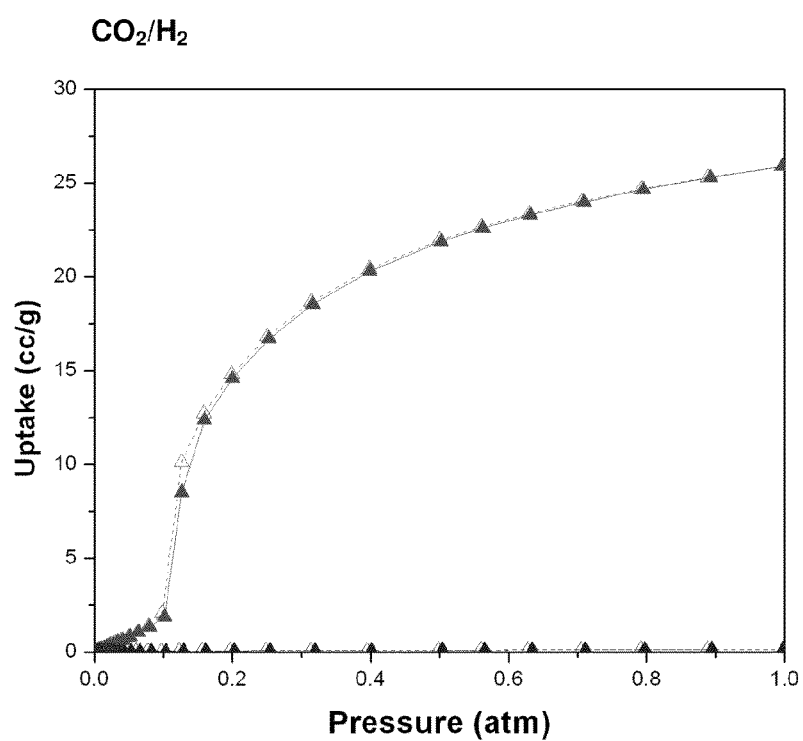
Figure 5:
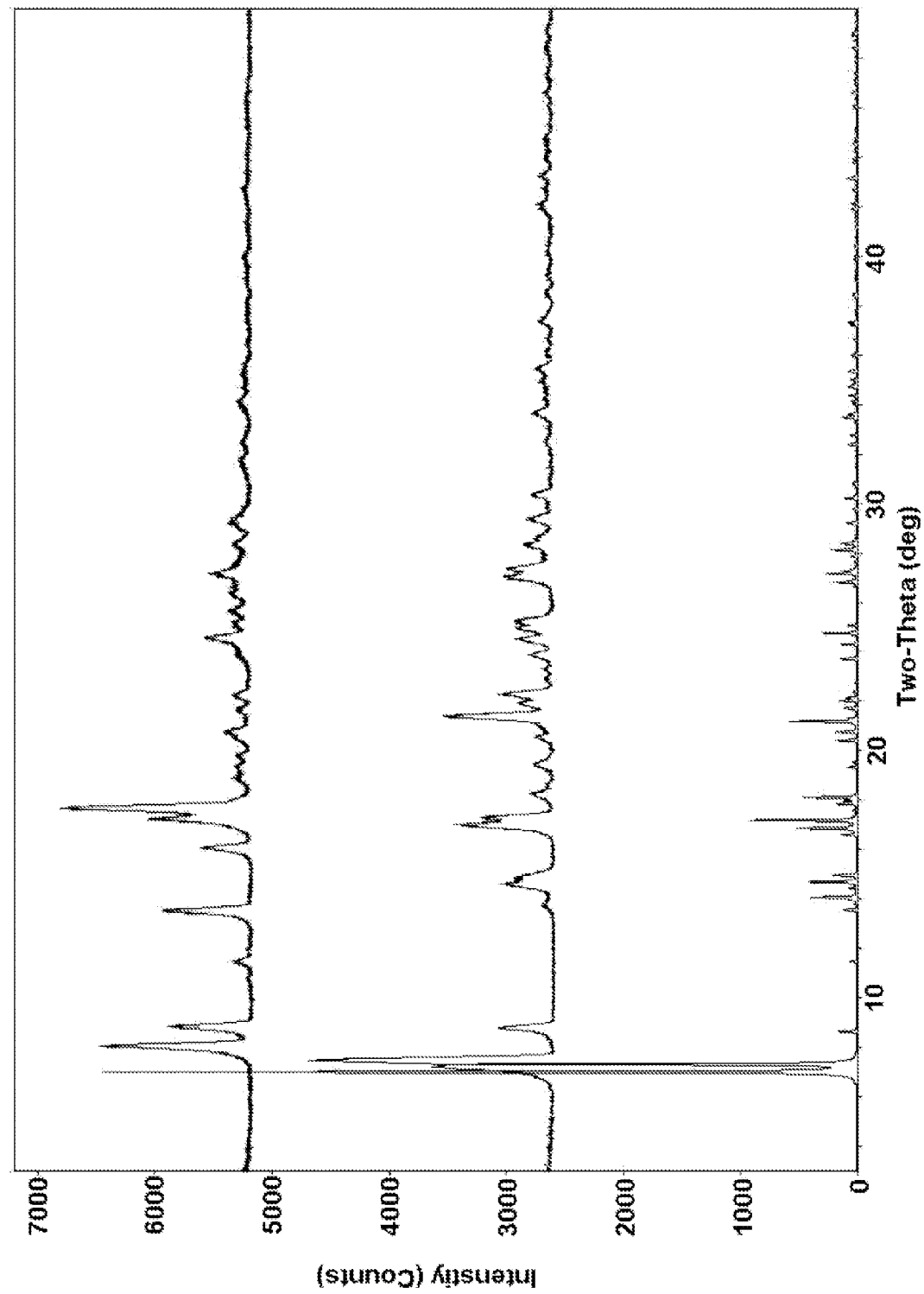
FIG. 5 (Top) depicts PXRD patterns of the compound of FIG. 1, wherein simulated is in blue, as-made in green, and out-gassed (after removal of guest molecules) in red, in which a structure change is evident from the changes in the PXRD peaks; and (Bottom) depicts the shifting of low angle peaks after guest removal.
Figure 5:
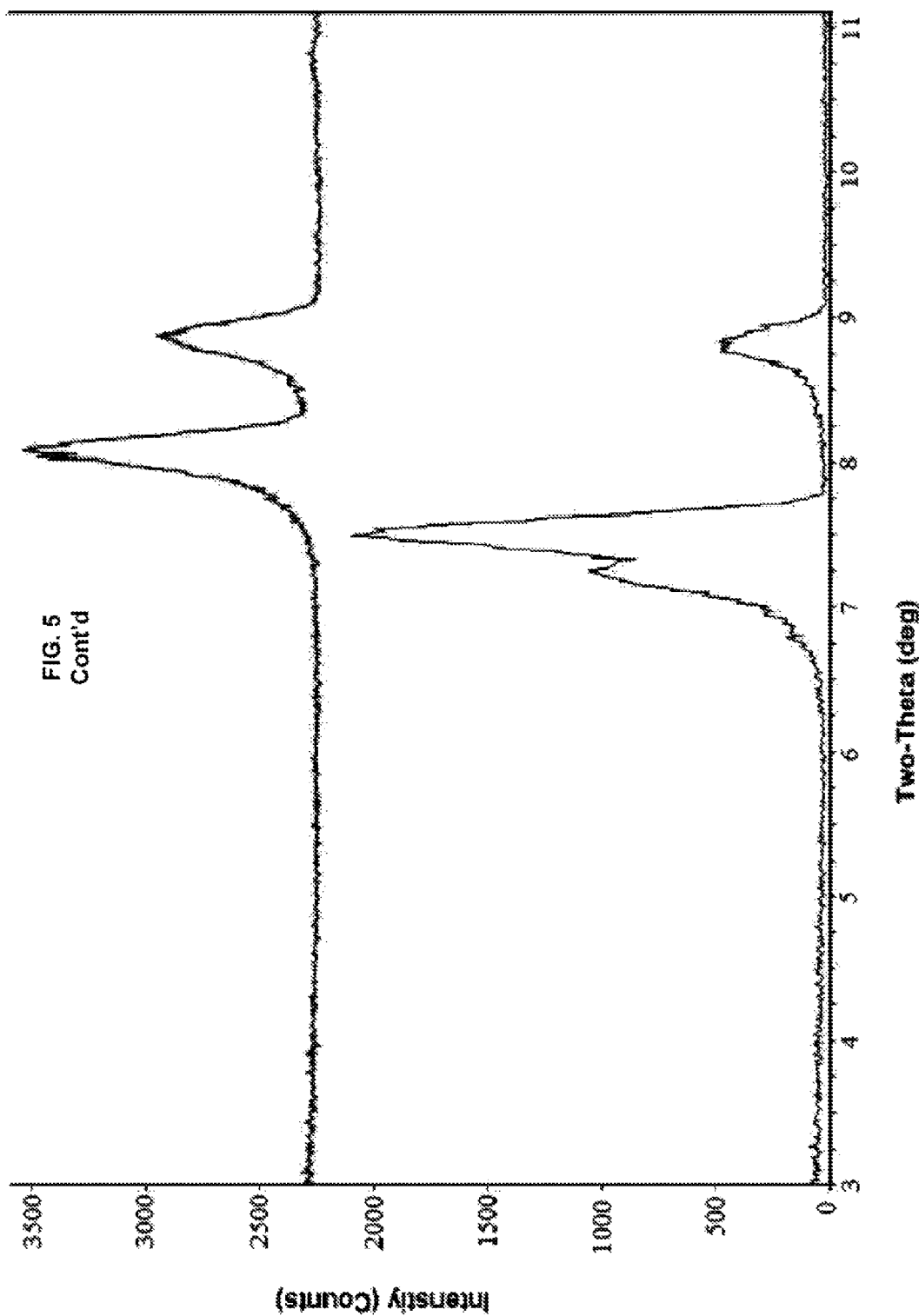
Figure 6:
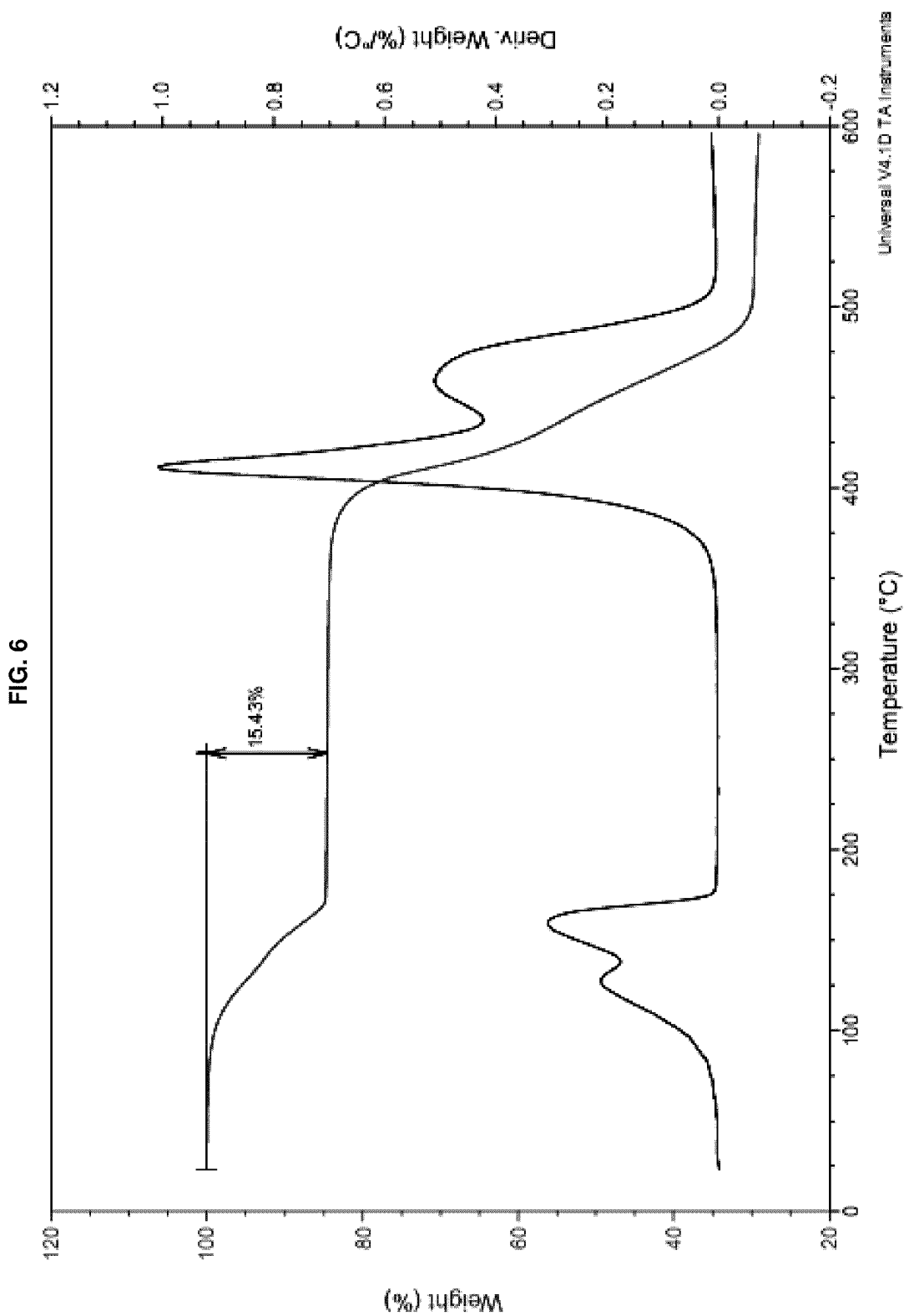
FIG. 6 depicts the $T_g$ of the compound of FIG. 1.
Figure 7:
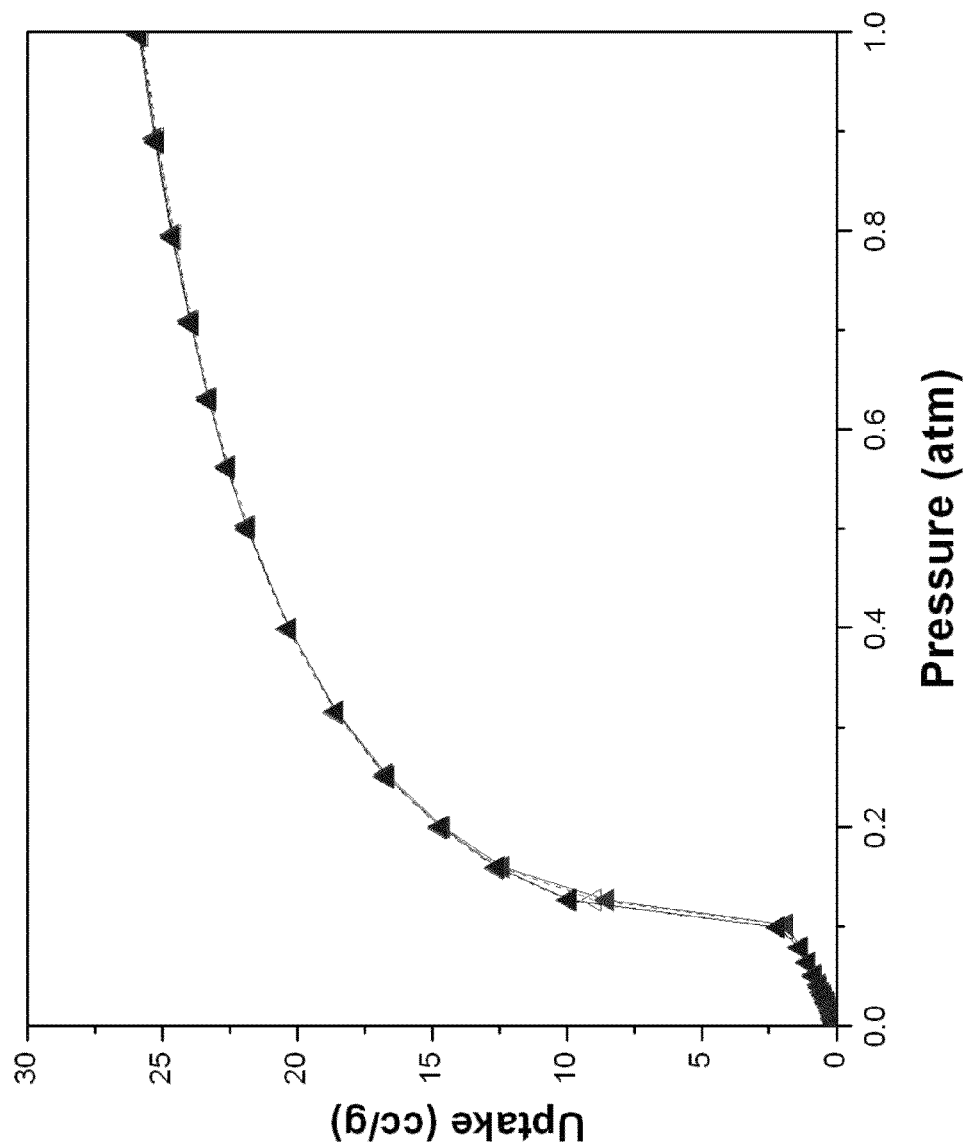
FIG. 7 depicts repetitive runs of $CO_2$ adsorption-desorption isotherms at 25° C. up to 1 atm (Blue: first run, Red: second run)
Figure 8:
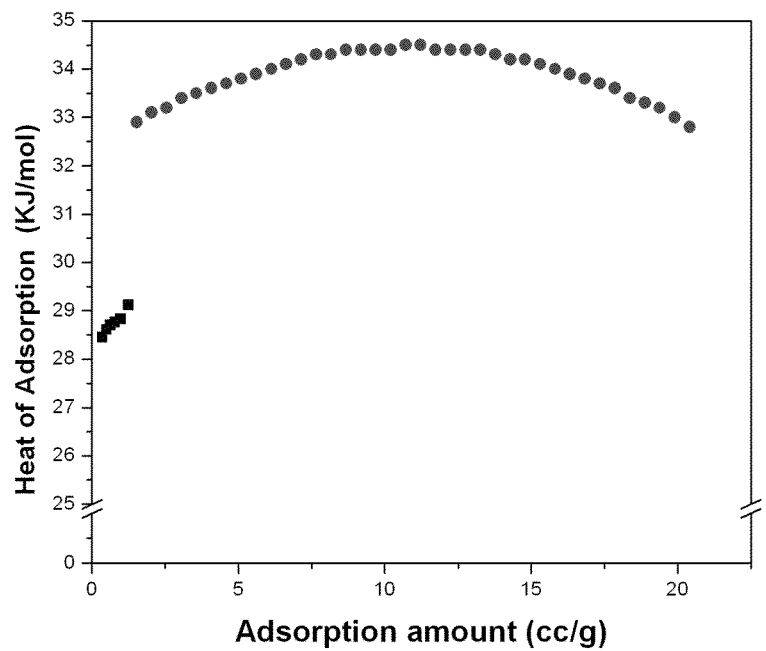
FIG. 8 depicts heats of $CO_2$ adsorption as a function of uptake.

The out-gassing procedure was repeated on the same sample between experiments for 0.5~1 hour. Pore properties (e.g. pore volume, pore size, and surface area) were analyzed using Autosorb v1.50 software. The adsorption-desorption isotherms of Ar (87K) and $N_2$ (77K) are plotted in FIGS. 4A and 4B, respectively. PXRD patterns of the simulated, as-made and out-gassed samples are shown in FIG. 5. TGA analysis indicated a weight loss of 15.43 wt % in the temperature range of 80-140° C., in excellent agreement with the calculated percentage weight of guest DMF molecules, 15.6%. Plotted in FIG. 7 are two repetitive runs of $CO_2$ isotherms taken at 25° C. Comparisons of $CO_2$ with $H_2$, $CH_4$ and CO adsorption-desorption isotherms at 25° C. up to 1 atm are shown in FIGS. 3E, 3B and 3C, respectively. $CO_2$ isotherms taken at three different temperatures (5, 15 and 25° C.) are depicted in FIG. 9.

3. Breakthrough Experiments

Figure 11:
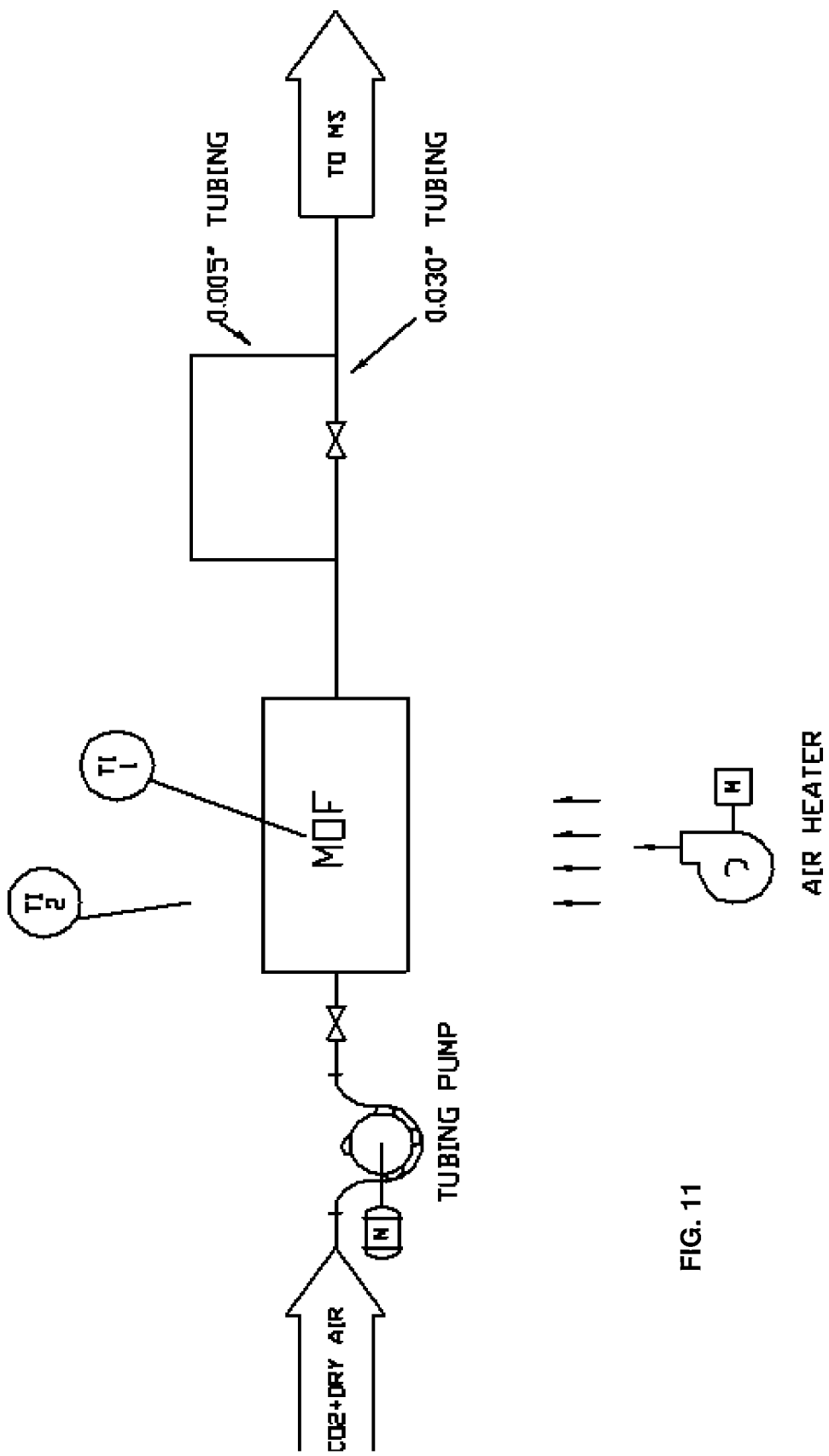
FIG. 11 depicts the equipment flow diagram for the breakthrough experiments.

In a breakthrough experiment a vacuum of 3 kPa was applied to an activated sample of the FIG. 1 compound and the off-gas analyzed using a Residual Gas Analyzing Mass Spectrometer (RGA). A mixture of $CO_2$ in air was delivered to the sample-containing test cell with the outlet valve closed but bleeding off a fraction of the gas through the small diameter tube (127 μm) to the RGA (FIG. 11). The $CO_2$ fraction was 30% for the control (FIG. 7). For all other conditions $CO_2$ was held at 20%. The gas feed flow rate was 5.7 scc/m. Flow continued until the pressure in the test cell reached steady state (~80 kPa). At this time the feed valve was closed (time 0:00); the gas bleed continued until the pressure reached a value of 10-12 kPaa. At this time the valve to the larger diameter tubing (762 μm) was opened allowing the pressure to drop more rapidly.

Figure 12:
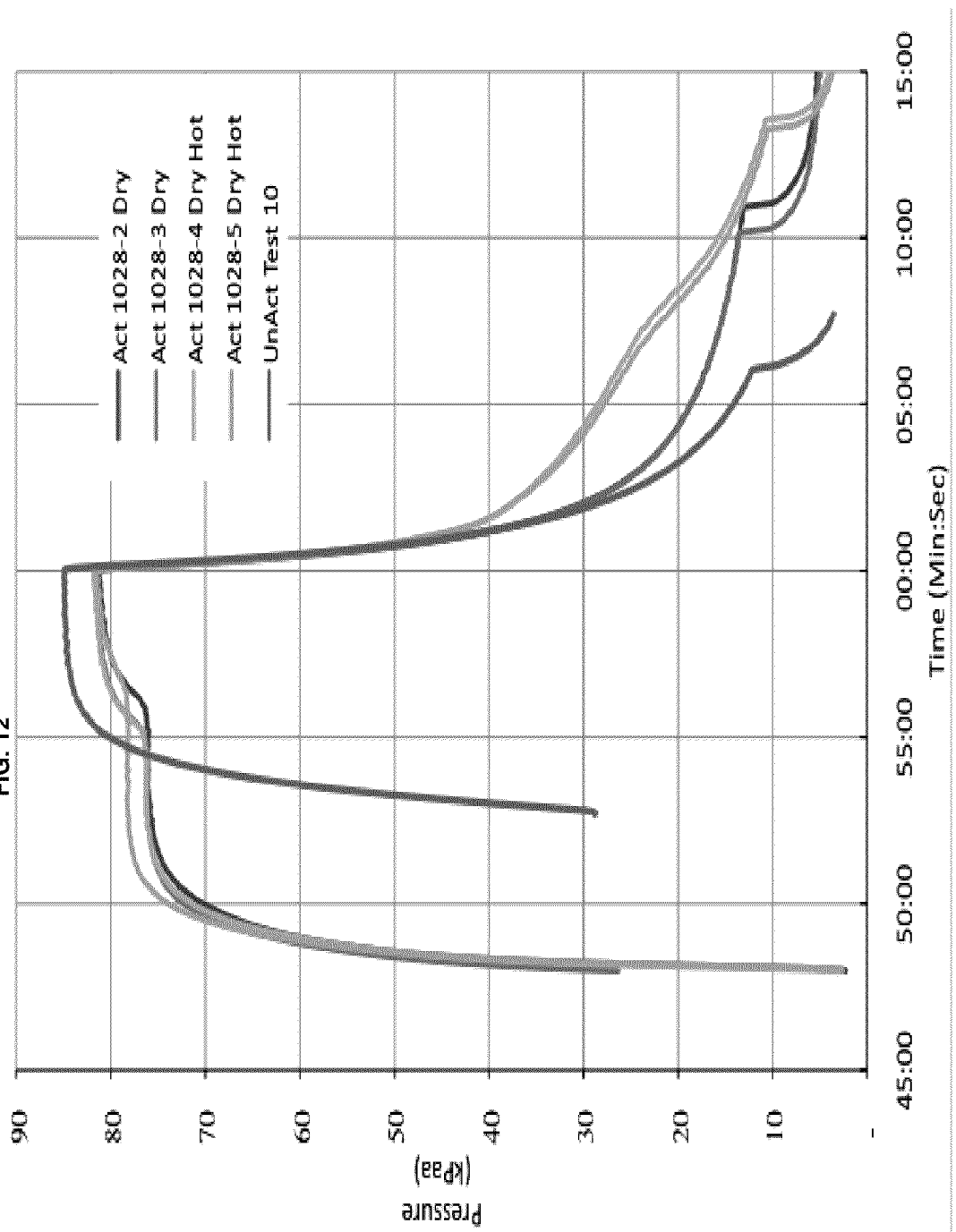
FIG. 12 depicts pressure in an activated compound according to FIG. 1 at 24° C. with 15% $CO_2$ in air for load and unload.
Figure 13:
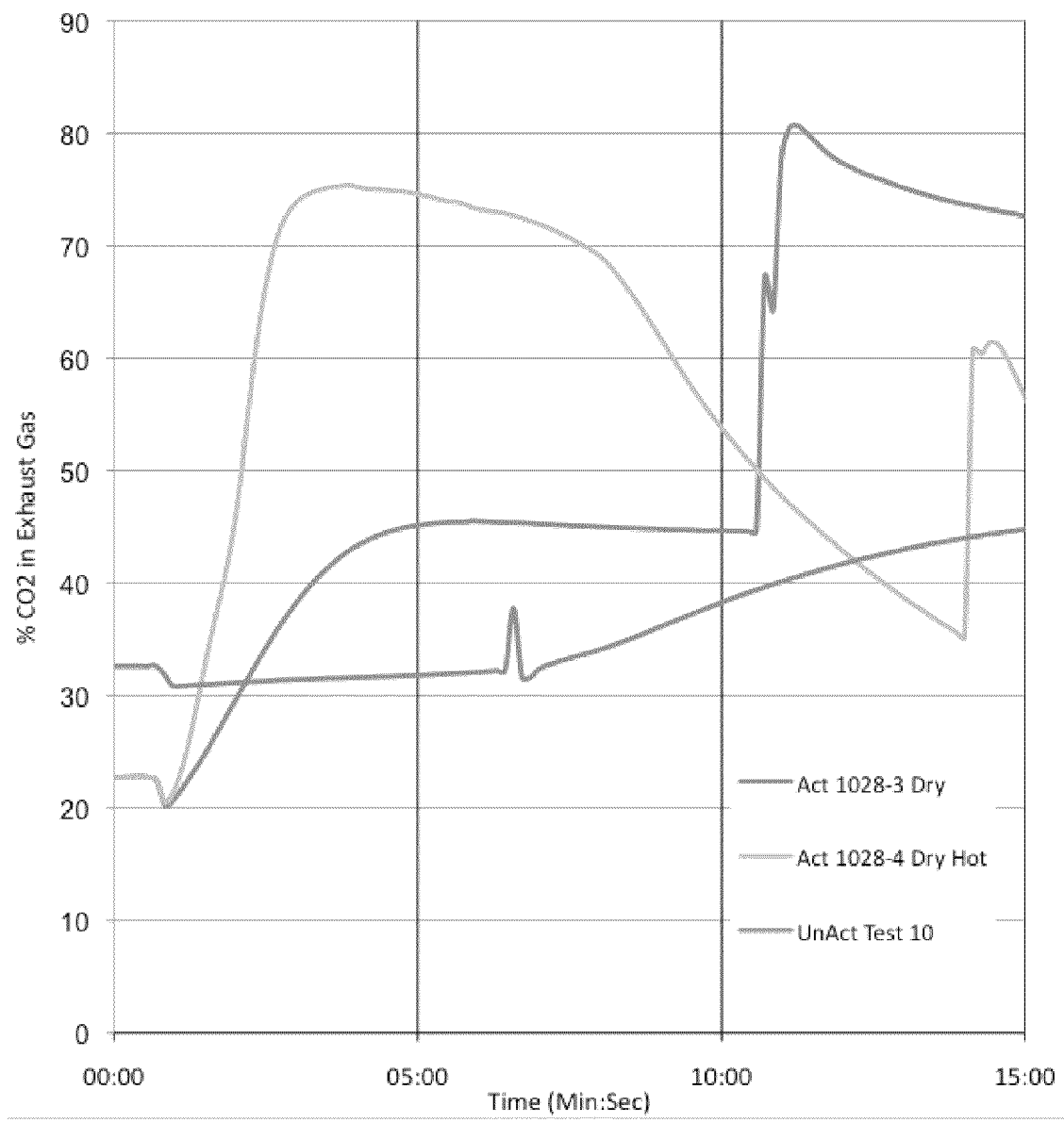
FIG. 13 depicts $CO_2$ composition of exhaust from an activated compound according to FIG. 1.

The adsorption behavior of the compound of FIG. 1 to the introduced air/$CO_2$ mixture can be illustrated by three different graphs: pressure vs. time (FIG. 12), composition vs. time (FIG. 7) and partial pressure of $CO_2$ vs. time (FIG. 13). FIG. 12 shows that the pressure increases rapidly as the compound of FIG. 1 is loaded. $CO_2$ breakthrough is indicated by the shoulder visible between time 55:00 and 0:00. The unactivated compound of FIG. 1 (blue) allows the gas to exit rapidly. In contrast, the activated compound of FIG. 1 releases the $CO_2$ more slowly (red and tan lines). The entire cycle from start to finish is typically complete in less than 30 minutes; a 12 min load and 15 min unload.

The difference in adsorption performance between the activated and unactivated compounds of FIG. 1 is apparent as the pressure falls. The pressure drops more rapidly for the non-activated material showing little adsorption. It falls more slowly for the activated form indicating adsorbed gas is being released, thus extending the time at the higher pressure.

Quickly heating the sample to 50° C. promoted release of the $CO_2$. In FIGS. 7, 12 and 13, heating was initiated at time 0. In FIG. 12 there was an initial load rate 5.7 scc/m with 0.5 g of activated compound in a tube of 127 μm in diameter. Multiple runs indicate the consistency of performance. In FIG. 13 there is a distinct increase in the length of time that the pressure remains high for the heated compound of FIG. 1, indicating rapid desorption yielding higher pressures. In FIG. 7, there is a much more rapid increase in the concentration of $CO_2$ and in FIG. 13 the PP of $CO_2$ increases to a much higher level (25 kPaa) than the inlet PP (~18 kPaa). This is an important indicator that the $CO_2$ may be able to be recovered economically.

The recovered carbon dioxide can be stored. Various forms of storage sites have been conceived for permanent storage of carbon dioxide. Examples of storage forms include gaseous storage in various deep geological formations, liquid storage in the ocean, and solid storage by reaction of carbon dioxide with metal oxides to produce stable carbonates. Examples of geological storage locations include oil and gas fields, deep saline formations and coal seams.

Carbon dioxide storage has been carried out for more than ten years in demonstration plants in Sleipner, in the Norwegian part of the North Sea and in Otway, Australia where close monitoring is carried out to study the effect of carbon dioxide storage. Carbon dioxide has also been stored in mature oil and gas fields in enhanced oil recovery (EOR) projects in North America for many decades.

In summary, the compound of FIG. 1C demonstrates exceptionally high selectivity in capturing and separating carbon dioxide from a gas mixture that mimics the composition of flue gases emitted from power plant. The adsorption study of other small gases, including $H_2$, CO and $CH_4$ also reveals that the compound is highly selective in taking up $CO_2$.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed is:

1. A method of separating carbon dioxide from a mixture of gases, the method comprising the steps of:
  a) passing the gas mixture through a porous three-dimensional polymeric coordination compound characterized by a plurality of layers comprising two-dimensional arrays of repeating structural units, each repeating structural unit comprising at least one transition or post-transition metal atom or cation coordinated to:
   (1) at least one binding member of a bidentate binding site on each of two polyfunctional ligands of Formula I

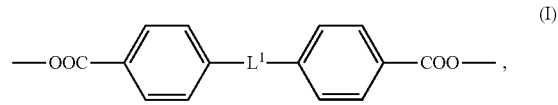

wherein $L^1$ is a bond or a linker, said linker being linear or ring, substituted or non-substituted, saturated or unsaturated group comprising between 1 and 6 atoms independently selected from the group consisting of C, N and S; and
   (2) one binding site of a bis-pyridine exodentate bridging ligand of Formula II:

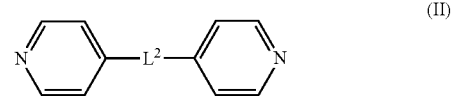

wherein $L^2$ is a bond or a linear, substituted or non-substituted, saturated or unsaturated linker containing between 2 and 6 atoms independently selected from the group consisting of C, N and S; and
  wherein:
   (i) at least one binding member of a second bidentate binding site on each polyfunctional ligand is further coordinated to at least one transition metal atom or cation in a different repeating structural unit within the same layer containing a two-dimensional array of repeating structural units;
   (ii) the exodentate bridging ligand extends essentially perpendicularly from a plane defined by said layer containing a two-dimensional array of repeating structural units to further coordinate with a transition metal atom in a repeating structural unit in an adjacent layer; and
   (iii) the ligands of the three-dimensional polymeric compound define channels and pores of molecular size throughout the structure of the compound; and (b) recovering the resulting mixture, wherein the resulting mixture has a decreased carbon dioxide content.

2. The method of claim 1, wherein $L^1$ and $L^2$ are each independently a bond, —CH=CH— or —CH$_2$—CH$_2$—.

3. The method of claim 1, wherein $L^1$ is a bond; and $L^2$ is —CH=CH— or —CH$_2$—CH$_2$—.

4. The method of claim 1, wherein the transition metal is zinc.

5. The method of claim 1, wherein step (a) is conducted at a pressure of greater than 0.1 atm.

6. The method of claim 1, wherein step (a) is conducted at a pressure of about 1 atm.

7. The method of claim 1, wherein said mixture of gases comprises at least one gas selected from hydrogen, oxygen, nitrogen, carbon monoxide, and methane.

8. The method of claim 1, wherein said mixture of gases is an industrial flue gas.

9. The method of claim 1, further comprising a step of (c) recovering carbon dioxide retained in the microporous three-dimensional polymeric coordination compound.

10. The method of claim 9, wherein said recovering comprises heating the polymeric coordination compound containing carbon dioxide to an elevated temperature until the carbon dioxide is released, and collecting the carbon dioxide released from the polymeric coordination compound.

11. The method of claim 1, further comprising repeating step (a).

12. A method of adsorbing carbon dioxide, comprising exposing a composition comprising carbon dioxide to a three-dimensional polymeric coordination compound characterized by a plurality of sheets comprising a two-dimensional array of repeating structural units, each repeating structural unit comprising at least one transition metal atom coordinated to: a) one binding site of an exodentate bridging ligand; and b) at least one binding member of a bidentate binding site on each of two biaryl-dicarboxylate ligands, wherein:

(1) at least one binding member of a second bidentate binding site on each said biaryl-dicarboxylate ligand is further coordinated to at least one transition metal atom in a different repeating structural unit within the same said sheet containing as two-dimensional array of repeating structural units;

(2) the exodentate bridging ligand extends essentially perpendicularly from a plane characteristic of said sheet containing a two-dimensional array of repeating structural units to further coordinate with a transition metal atom in a repeating structural unit in an adjacent sheet;

(3) the exodentate ligand is a ligand that comprises at least two monodentate binding sites, wherein the biaryl-dicarboxylate ligand compounds and the exodentate ligand compounds are selected so that the ligands of the three-dimensional polymeric compound define channels and pores of molecular size throughout the structure of the compound capable of adsorbing carbon dioxide.

13. The method of claim 12, wherein the repeating structural unit of the compound has the stoichiometric formula $[M_a(pbd)_b(ed)_f]$, optionally comprising one or more solvent molecules characterized by formula $[M_a(pbd)_b(ed)_f]\cdot n(sol)$, wherein:

"pbd" is a biaryl-dicarboxylate ligand;

"ed" is an exodentate ligand having at least two monodentate binding sites;

"M" is a transition or post-transition metal having at least one stable oxidation state capable of forming stable bonds with said biaryl-dicarboxylate and exodentate ligands;

"sol" is a solvent molecule;

"a", "b", and "f" are independently integers selected from 1 to 3;

n is a number between 0-3; and the coordinate space occupied by the "pbd" and "ed" ligands is equal to a stable coordination number of "a" number of transition or post-transition metal (M) atoms or cations.

14. The method of claim 13, wherein the exodentate ligand is a ligand having two monodentate binding sites.

15. The method of claim 13, wherein said biaryl-dicarboxylate has a structure of formula I:

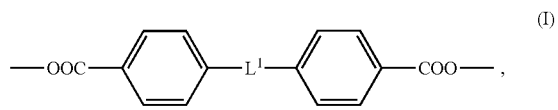

(I)

wherein $L^1$ is a bond or a linker, the linker being linear or ring, substituted or non-substituted, saturated or unsaturated group comprising between 1 and 6 atoms independently selected from the group consisting of C, N and S.

16. The method of claim 15, wherein $L^1$ is a bond, —CHR$^1$—, —CHR$^1$—CHR$^2$—, —CR$^1$=CR$^2$—, or —C≡C—, wherein R$^1$ and R$^2$ are each independently hydrogen (H), halogen, hydroxyl, or methyl.

17. The method of claim 13, wherein said exodentate bridging ligand is a bis-pyridine compound of Formula II:

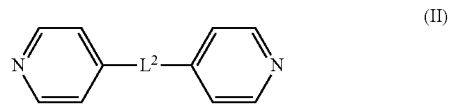

(II)

wherein $L^2$ is a bond or a linear, substituted or non-substituted, saturated or unsaturated linker containing between 1 and 6 atoms independently selected from the group consisting of C, N and S, wherein the nitrogen (N) atoms of the two pyridine rings are two binding sites.

18. The method of claim 17, wherein $L^2$ is a bond, —CHR$^2$—,—CHR$^1$—CHR$^2$—, —CR$^1$=CR$^2$—, or —C≡C—, wherein R$^1$ and R$^2$ are each independently hydrogen (H), halogen, hydroxyl, or methyl.

19. The method of claim 13 wherein: "M" is zinc or cadmium, "pbd" is biphenyl-4,4'-dicarboxylate ("bpdc"), "ed" is selected from 4,4'-bipyridine ("bp"), 1,2-bis(4-pyridyl)ethylene ("bpee") or 1,2-bis(4-pyridyl)ethane ("bpe"), "sol" is dimethylformamide (DMF), "a" is 2, "b" is 2, "f" is 1, and n is 0 or 2.

20. The method of claim 13, wherein "M" is $Zn^{2+}$, "pbd" is biphenyl-4,4'-dicarboxylate ("bpdc"), "ed" is 1,2-bis(4-pyridyl)ethylene ("bpee"), "Sol" is dimethylformamide (DMF), "a" is 2, "b" is 2, "f" is 1, and n is 2, wherein the compound comprises a flexible, porous three-dimensional network composed of one-dimensional open channels running along crystallographic b-axis.

* * * * *